United States Patent
Wang et al.

(10) Patent No.: US 11,149,322 B2
(45) Date of Patent: Oct. 19, 2021

(54) METHODS AND COMPOSITIONS FOR HUMAN PAPILLOMAVIRUSES AND SEXUALLY TRANSMITTED INFECTIONS DETECTION, IDENTIFICATION AND QUANTIFICATION

(71) Applicant: Chapter Diagnostics, Inc., Menlo Park, CA (US)

(72) Inventors: Chunlin Wang, Menlo Park, CA (US); Zhihai Ma, Mountain View, CA (US); Baback Gharizadeh, Menlo Park, CA (US)

(73) Assignee: Chapter Diagnostics, Inc., Menlo Park, CA (US)

( * ) Notice: Subject to any disclaimer, the term of this patent is extended or adjusted under 35 U.S.C. 154(b) by 0 days.

(21) Appl. No.: 16/435,017

(22) Filed: Jun. 7, 2019

(65) Prior Publication Data
US 2020/0385821 A1 Dec. 10, 2020

(51) Int. Cl.
| | |
|---|---|
| *C12Q 1/68* | (2018.01) |
| *C12Q 1/6881* | (2018.01) |
| *C12Q 1/6883* | (2018.01) |
| *C12Q 1/6886* | (2018.01) |
| *C12N 15/10* | (2006.01) |
| *C12Q 1/70* | (2006.01) |

(52) U.S. Cl.
CPC ......... *C12Q 1/708* (2013.01); *C12Q 2600/16* (2013.01)

(58) Field of Classification Search
CPC .. C12Q 1/6881; C12Q 1/6883; C12Q 1/6886; C12Q 2600/118; C12Q 2600/156
See application file for complete search history.

(56) References Cited

U.S. PATENT DOCUMENTS

| | | | |
|---|---|---|---|
| 9,918,702 B2 * | 3/2018 | Tariyal | A61B 5/157 |
| 2012/0004113 A1 | 1/2012 | Moon | |
| 2013/0149697 A1 | 6/2013 | Hudson et al. | |
| 2013/0184164 A1 | 7/2013 | Moon et al. | |
| 2016/0201124 A1 | 7/2016 | Donahue et al. | |
| 2019/0078142 A1 | 3/2019 | Apte et al. | |

FOREIGN PATENT DOCUMENTS

| | | | |
|---|---|---|---|
| WO | WO2002034939 | * | 5/2002 |
| WO | WO2017142989 | * | 8/2017 |

OTHER PUBLICATIONS

Barzon L et al, Human papillomavirus genotyping by 454 next generation sequencing technology, J Clin Virol. Oct. 2011; 52(2):93-7.
Cornall AM et al, In vitro assessment of the effect of vaccine-targeted human papillomavirus (HPV) depletion on detection of non-vaccine HPV types: Implications for post-vaccine surveillance studies, J Virol Methods. Mar. 2015; 214:10-4.
Cuzick J, Need for expanded HPV genotyping for cervical screening, Papillomavirus Res. Dec. 2016; 2:112-115.
De Roda Husman AM et al, The use of general primers GP5 and GP6 elongated at their 3' ends with adjacent highly conserved sequences improves human papillomavirus detection by PCR, J Gen Virol. Apr. 1995; 76 (Pt 4):1057-62.
Gravitt PE, et al, Improved Amplification of Genital Human Papillomaviruses, J Clin Microbiol. Jan. 2000; 38(1):357-61.
Jemal A et al, Cancer Statistics, 2008, CA Cancer J Clin. Mar.-Apr. 2008; 58(2):71-96.
Joura, Attribution of 12 High-Risk Human Papillomavirus Genotypes to Infection and Cervical Disease, Cancer Epidemiol Biomarkers Prev. Oct. 2014; 23(10):1997-2008.
Moberg M et al, High viral loads of human papillomavirus predict risk of invasive cervical carcinoma, Br J Cancer. Mar. 14, 2005; 92(5):891-4.
Muñoz N et al, The causal link between human papillomavirus and invasive cervical cancer: A population-based case-control study in Colombia and Spain, Int J Cancer. Nov. 11, 1992; 52(5):743-9.
Muñoz N et al, Epidemiologic Classification of Human Papillomavirus Types Associated with Cervical Cancer, N Engl J Med. Feb. 6, 2003; 348(6):518-27.
Trevisan A et al, Human papillomavirus type 16 viral load measurement as a predictor of infection clearance, J Gen Virol. Aug. 2013; 94(Pt 8):1850-7.
Vos T. et al, Global, regional, and national incidence, prevalence, and years lived with disability for 310 diseases and injuries, 1990-2015: a systematic analysis for the Global Burden of Disease Study 2015, Lancet. Oct. 8, 2016; 388 (10053):1545-1602.
Walboomers JM, Human papillomavirus is a necessary cause of invasive cervical cancer worldwide, J Pathol. Sep. 1999; 189(1):12-9.
Wright, T.C. et al, 2001 Consensus Guidelines for the Management of Women With Cervical Cytological Abnormalities, JAMA. Apr. 24, 2002; 287(16):2120-9.
Xi LF et al, Viral Load in the Natural History of Human Papillomavirus Type 16 Infection: A Nested Case-Control Study, J Infect Dis. May 15, 2011; 203(10):1425-33.

* cited by examiner

*Primary Examiner* — Barry A Chestnut
(74) *Attorney, Agent, or Firm* — Maynard Cooper & Gale, P. C.; Matthew J. Parker (57) ABSTRACT

The present disclosure relates to compositions and methods for detection, identification and quantification of human papillomaviruses (HPV) and clinically significant sexually transmitted infections (STI) in a single amplification reaction. The disclosed method utilizes next-generation sequencing (NGS) to sequence amplified products. The present disclosure is also directed to kits containing primers specific to multiple HPV and STI targets.

5 Claims, 7 Drawing Sheets

| Sample ID | GAPDH | HPV16 | HPV18 | HPV31 | HPV35 | HPV39 | HPV45 | HPV51 | HPV52 | HPV56 | HPV59 | HPV6 | HPV68a | HPV68b | Results |
|---|---|---|---|---|---|---|---|---|---|---|---|---|---|---|---|
| 1 | 10,000 | 0 | 0 | 0 | 0 | 0 | 0 | 0 | 0 | 310 | 0 | 0 | 0 | 0 | HPV56 |
| 2 | 10,000 | 0 | 0 | 0 | 0 | 0 | 0 | 0 | 0 | 0 | 230 | 0 | 0 | 0 | HPV59 |
| 3 | 10,000 | 0 | 0 | 0 | 0 | 0 | 0 | 0 | 0 | 0 | 0 | 0 | 692 | 0 | HPV68a |
| 4 | 10,000 | 328 | 183 | 0 | 0 | 0 | 0 | 372 | 0 | 0 | 0 | 322 | 0 | 0 | HPV6, 16, 18, 51 |
| 5 | 10,000 | 0 | 0 | 0 | 0 | 0 | 0 | 0 | 0 | 0 | 0 | 414 | 0 | 0 | HPV6 |
| 6 | 10,000 | 0 | 1 | 0 | 0 | 0 | 249 | 0 | 0 | 0 | 0 | 0 | 0 | 0 | HPV45 |
| 7 | 10,000 | 0 | 0 | 0 | 308 | 0 | 0 | 0 | 0 | 307 | 142 | 0 | 570 | 0 | HPV35, 56, 59. 68a |
| 8 | 10,000 | 0 | 0 | 0 | 0 | 0 | 0 | 266 | 0 | 0 | 0 | 0 | 0 | 0 | HPV51 |
| 9 | 10,000 | 0 | 0 | 0 | 0 | 154 | 0 | 0 | 0 | 0 | 0 | 0 | 0 | 0 | HPV39 |
| 10 | 10,000 | 0 | 0 | 0 | 175 | 0 | 0 | 0 | 0 | 0 | 0 | 0 | 0 | 0 | HPV35 |
| 11 | 10,000 | 0 | 4 | 0 | 0 | 280 | 137 | 0 | 711 | 0 | 0 | 0 | 0 | 500 | HPV39, 45, 52, 68b |
| 12 | 10,000 | 0 | 0 | 215 | 0 | 0 | 0 | 0 | 0 | 1 | 0 | 0 | 0 | 0 | HPV31 |
| 13 | 10,000 | 0 | 0 | 0 | 0 | 0 | 0 | 0 | 542 | 0 | 0 | 0 | 0 | 0 | HPV52 |

Figure 7

| Sample ID | GAPDH | HSV6 | HSV11 | HPV16 | HPV18 | HPV31 | HPV35 | HPV39 | HPV45 | HPV51 | HPV52 | HPV53 | HPV56 | HPV59 | CT | HSV2 | MG | MH | NG | UP |
|---|---|---|---|---|---|---|---|---|---|---|---|---|---|---|---|---|---|---|---|---|
| 1 | 10,000 | | 210,421 | 634 | 6,604 | | | | 2,917 | 4,967 | | | | | | | 523 | | | 3,926 |
| 2 | 10,000 | | | | 56,050 | | | | | | | | | | | | | | | |
| 3 | 10,000 | | | 4,981 | | | | | | 1,470,862 | | | | | | | | | | |
| 4 | 10,000 | | | 7,099 | | 21,851 | | | | | | 4,269 | | | 1,845 | | | | | |
| 5 | 10,000 | | | | | | | | | 162,776 | | | | | | | | | | |
| 6 | 10,000 | | | 65,315 | | | | | | | 285,136 | | | | | | | | | |
| 7 | 10,000 | | | | | 161,760 | | | | 147 | | | | | | | | 15,774 | | |
| 8 | 10,000 | | | | | | | | | | | | 40,042 | | | | | | 12,828 | |
| 9 | 10,000 | | | | | | | 345,160 | | 558,465 | 715,671 | | | 862 | | | | 338,572 | | 946 |
| 10 | 10,000 | | | | | | | 7,118 | | | | | | | | 154,553 | | | | |
| 11 | 10,000 | | | 253,619 | | | | | | | | | | | | 293,102 | | | | |
| 12 | 10,000 | | 3,129 | | | | | | | | | | | | | | | | | |
| 13 | 10,000 | 7,471,982 | 506 | 1,233 | | | | | | | | | | | | | | | | 2,114 |

Human Papillomavirus (HPV)
Chlamydia trachomatis (CT)
Herpes Simplex 2 (HSV2)
Mycoplasma genitalium (MG)
Mycoplasma hominis (MH)
Neisseria gonorrhoeae (NG)
Ureaplasma parvum (UP)

METHODS AND COMPOSITIONS FOR HUMAN PAPILLOMAVIRUSES AND SEXUALLY TRANSMITTED INFECTIONS DETECTION, IDENTIFICATION AND QUANTIFICATION

BACKGROUND OF THE INVENTION

Sexually transmitted infections (STIs) impose a huge disease burden globally and cause diseases, such as cancer, which can lead to mortality. The burden on the healthcare system and healthcare expenditure is substantial. Worldwide, STIs are mainly caused by seven infections: syphilis, gonorrhea, chlamydia, trichomoniasis, genital herpes, hepatitis B virus (HBV), and human papillomavirus (HPV). Many of these infections are often symptom-free and silent. However, STIs sometimes result in serious and fatal health consequences. For example, certain HPV types cause cervical cancer, with a global prevalence of over 530,000 cervical cancer incidents and over 250,000 mortality per year (Jemal A et al, CA Cancer J Clin. 2008 March-April; 58(2):71-96). Treponema pallidum causes syphilis, which, among pregnant women, results in up to 1.5 million perinatal deaths each year. Gonorrhea and chlamydia can damage the fallopian tubes, which can cause infertility as well as tubal pregnancy, an important cause of maternal death. In addition, genital herpes and other genital ulcer diseases increase the risk of HIV transmission.

HPV is the direct causative agent of cervical cancer and it has been detected in 99.7% of cervical cancers (Munoz N et al, Int J Cancer. 1992 Nov. 11; 52(5):743-9, Walboomers J M, J Pathol. 1999 September; 189(1):12-9). HPV has also been detected in other cancers such as oropharyngeal, vaginal, vulvar, anal and penile cancers. HPV is a double-stranded circular DNA virus and has a genome of about 8000 base pairs. The HPV genome comprises eight protein-coding genes that are divided into early and late genes: L1 and L2 encode capsid proteins, E1 and E2, E4, E5, E6 and E7 encode proteins that are involved in replication, transcription and transformation, and also play a role in driving cell cycle entry, immune evasion and virus release. HPV is divided into low-risk and high-risk types or genotypes based on benign, premalignant and malignant lesions. Only a small fraction of those infected with high-risk HPV, however, will develop cancer.

Cervical cancer is among one of the most preventable cancers. Historically, cytology screening or Pap test has been the primary screening for cervical cancer, which is a visual, subjective search for abnormal cell transformations. Organized cervical cancer screening programs have saved the lives of a great number of women. Further, organized cytology screening programs have effectively reduced the burden of disease associated with HPV, and the introduction of sensitive molecular methods have assisted with the detection of the HPV virus, significantly improving the efficiency of screening programs (Wright, T. C. et al, JAMA. 2002 Apr. 24; 287(16):2120-9). Detection of transient HPV infections causes unnecessary follow-ups, treatment and costly medical procedures. Therefore, the goal of cervical cancer screening is to detect pre-cancer and cancer rather than transient HPV infections.

STIs are among the most common diseases globally. In 2015, about 1.1 billion people had STIs (HIV not included), of which about: 500 million were infected with either syphilis, gonorrhea, chlamydia or trichomoniasis; 530 million were infected with genital herpes; and 290 million women were infected with HPV (Vos T. et al, Lancet. 2016 Oct. 8; 388(10053):1545-1602). In the United States, there were 19 million new cases of sexually transmitted infections in 2010.

To date, there are over 200 HPV types identified and more than 40 infect human anogenital tract (Muñoz N et al, N Engl J Med. 2003 Feb. 6; 348(6):518-27). They are categorized into two groups of high-risk and low-risk. There is general agreement that only high-risk types cause cervical cancer and that low-risk types cause genital warts. In HPV classification, a sequence similarity under 90% is considered a new HPV type, homology between 90% and 98% constitute a subtype, and a homology above 98% represents a type variant. There is a consensus that 14 high-risk types are responsible for the majority of cervical cancers: HPV-16, 18, 31, 33, 35, 39, 45, 51, 52, 56, 58, 59, 66, 68a and 68b. Other types, however, are also reported to cause cervical cancer (Munoz N et al, N Engl J Med. 2003 Feb. 6; 348(6):518-27).

Multiplex PCR allows simultaneous amplification of many target genes by applying a combination of multiple target-specific primers to amplify multiple target regions of interest. Although use of multiple primers in PCR is very practical and reduces labor, cost and time, however, off-target amplifications or amplification artifacts such as primer-primer interactions (primer-dimers) may interfere with optimal amplification and further analysis such as sequencing. These artifacts use up PCR reaction reagents and generate shorter fragments instead of intended specific targets. These non-specific shorter fragments tend to dominate the amplification reaction as they are amplified more efficiently compared to the desired specific targets. These undesired artifacts might interfere with downstream procedures such as NGS. These artifacts may consume a sizeable portion of sequence reads, generating non-informative results.

In many biological applications, it can be very advantageous to increase the number of oligonucleotide primers to amplify as many possible targets in a single amplification reaction. By minimizing or circumventing primer-primer interactions and non-specific priming, more efficient multiplex PCR could be achieved. One approach is to develop selection methods based on mathematical algorithms to calculate primer interaction scores and select primer sequences with minimal interactions. Although this may be helpful, it may be compromised when increasing the number of primers in a PCR reaction.

The current PCR-based methods in HPV detection are analytically sensitive to the extent such methods can detect a few copies of target DNA. For detection of HPVs, there are two methods of HPV DNA amplification: 1) type-specific primer amplification, whereby each primer pair amplifies one specific HPV genotype; and 2) consensus/general primer amplification, which is a broad-spectrum HPV amplification, whereby multiple HPV types can be amplified in a single reaction by degenerate primers. Most consensus amplification methods use the L1 gene region as it contains conservative regions. The most used consensus primers are GP5+/GP6+, MY09/MY11, and PGMY09 (Gravitt P E, et al, J Clin Microbiol.2000 January; 38(1):357-61 and de Ruda Husman A M et al, J Gen Virol. 1995 April; 76 (Pt 4):1057-62).

The type-specific amplification detection approach detects individual genotype, and multiple reactions are needed to detect more genotypes or using multiplex real-time PCR, to detect more types in a reaction, which limits throughput. On the other hand, the consensus PCR has the advantage to detect multiple HPV types in a single reaction, but it may not amplify all the types uniformly and, moreover, a secondary method is needed to detect and identify specific genotypes. Consensus primer approach uses degenerate primers and relies on annealing to mismatch sites on HPV DNA types with substantial varying copy numbers, which can cause amplification biases. Due to the ease of use, many commercial assays use consensus detection approach (Barzon L et al, J Clin Virol. 2011 October; 52(2):93-7 and Cornall A M et al, J Virol Methods. 2015 March; 214:10-4.). The major drawback to consensus detection approach, however, is that consensus primers show poor detection of multiple co-infections due to HPV genotype suppression in PCR, where the dominance of one HPV genotype in a multiple co-infection can cause poor performance to detect lower levels of other co-existing genotypes. In general, the consensus broad-spectrum PCRs show poor performance because of genotype competition when mixed HPV genotypes are present in the same specimen. Many studies have shown that type-specific approach detects more HPV genotypes than the consensus detection approach due to unbalanced primer hybridization and annealing of consensus primers. Such uneven and biased amplification increases unbalanced sequencing of types in NGS, resulting in a higher cost and inaccurate results. The impact of assay design is crucial for analytical and clinical performance, especially to be able to detect accurately and uniformly mixed infections without any type suppression.

There is a clear difference in oncogenicity of each oncogenic genotype. Some genotypes in the high-risk HPVs are more oncogenic than the other. Thus, extended genotyping is important for patient management and triage. Many clinically validated HPV screening tests provide either no genotypes or partial genotypes mostly on only two types: HPV-16 and HPV-18. Many studies are reporting that knowledge of other types carry important clinical value for patient management and triage of HPV positive women. For example, studies demonstrate that HPV-31 and HPV-33 had the same or greater longitudinal risk as HPV18 over a 10-year period (Cuzick J, Papillomavirus Res. 2016 December; 2:112-115). Other HPV types that are significantly oncogenic and clinically relevant are HPV-31, 33, 45, 52, and 58 (Joura, Cancer Epidemiol Biomarkers Prev. 2014 October; 23(10)). Clearly, extended genotyping stratifies a woman's risk for pre-cancer and cancer and allows categorizing HPV genotypes with comparable risk, improving risk stratification and clinical management. Moreover, type-specific detection is a more accurate approach as it eliminates type suppression phenomenon caused by consensus degenerate PCR approaches.

HPV is a causative agent of cervical cancer, but the high prevalence of transient infections does not easily allow identification of women at higher risk of developing cervical cancer. Viral load has been suggested as a non-transient infection marker where high HPV load with normal cytology has been shown to be associated with the risk of developing dysplasia and carcinoma in situ (CIS). Strong association of HPV viral load with risk of persistent infection and pre-cancer has been reported in some studies correlating specific high-risk HPVs with pre-cancer and cancer. Many scientific reports have shown the association between viral load and cervical cancer severity, progression and development, indicating that the amount of HPV DNA increases proportionally with lesion severity and can even be detected before cervical lesions develop.

In another aspect, HPV viral load is a type-dependent risk marker for invasive carcinoma. In a study investigating the relation of HPV-16 viral load and persistent infections and progression to pre-cancer and cancer, (Fu LF et al J Infect Dis. 2011 May 15; 203(10):1425-33) it was reported that viral load of newly detected infections as well as changes in viral load predicts persistence and progression of HPV-16 infections, indicating that viral load of the newly detected HPV-16 infection correlated to consequences of the infection from a transient infection to a rapid progression to CIN3. Among those with a persistent HPV-16 infection, changes in viral load reflected risk of subsequent and/or underlying pre-cancer. Moreover, HPV viral load measurement has been shown to be a predictor of infection clearance (Trevisan A et al, J Gen Virol. 2013 August; 94(Pt 8):1850-7). To assess risk, longitudinal studies of viral load in the course of HPV infections could be a useful method monitoring cancer progression, although due to limitation of technologies there are not comprehensive studies of all types. HPV load provides information about the risk for subsequent development of pre-cancer and cancer, but the extent of progression correlates strongly with the HPV type (Moberg M et al, Br J Cancer. 2005 Mar. 14; 92(5):891-4). The quantification of viral load allows optimal balance between clinical sensitivity and specificity to detect precancer or cervical cancer, which in turn minimizes overtreatment and unnecessary follow-up procedures for high-risk HPV positive women without cervical lesions. Thus, there is a need for a screening method to accurately detect, identify and measure viral load of all the types to allow study of viral load and their correlation to pre-cancer and cancer.

Timely screening and detection minimizes the health and economic burden of STIs by virtue of allowing appropriate prevention and treatment. There remains a need for clinical methods of detecting, identifying and quantifying a broad spectrum of HPV and STIs in a rapid, accurate and cost-efficient manner. In addition, screening methods should involve a simple workflow and be easily automated.

SUMMARY OF THE INVENTION

In some embodiments, the present disclosure describes methods and compositions of amplifying selective target regions of HPV's genome and STIs in a nucleic acid sample. In some embodiments, the method comprises the steps of: 1) contacting the nucleic acid sample with target-specific primers in PCR reaction, in presence of barcoded universal primers; and 2) allowing primer extension to generate target amplification products (amplicons) of different sizes. In some embodiments, the method comprises the step of determining the presence or absence of target amplification product. In some embodiments, the method comprises the step of establishing the sequence the target amplification products. In some embodiments, less than 50, 40, 30, 20, 10, 5, 0.5, or 0.1% of the amplified products are primer-dimers or artifacts.

In some embodiments, the concentration of each target-specific primer can be about 500, 250, 100, 80, 70, 50, 30, 10, 2, or 1 nM. In some embodiments, the GC content of the target-specific primers can differ, and as an example it can be between 40% and 70%, or between 30% and 60% or 50% and 80%. In some embodiments, the melting temperature ($T_m$) of the target-specific primers can be between 55° C. and 65° C., or 40° C. and 70° C., or 55° C. and 68° C. In some embodiments, the length of the target-specific primers can be between 20 and 90 bases, 40 and 70 bases, 20 and 40 bases or 25 and 50 bases. In some embodiments, the 5'-region of the target-specific primer is a universal primer binding site that is not complementary or specific for any nucleic acid region in the sample. In some embodiments, the length of the target amplicons is between 50 and 500 bases, 90 and 350 bases, or 200 and 450 bases.

In various embodiments of any of the aspects of the present disclosure, the method of primer extension is based on the state-of-art polymerase chain reaction (PCR). In various embodiments, annealing time can be greater than 0.5, 1, 2, 5, 8, 10 or 15 minutes. In various embodiments, extension time can be greater than 0.5, 1, 2, 5, 8, 10 or 15 minutes.

High viral loads of HPV may predict risk of pre-cancer and cervical carcinoma. In some embodiments, the method disclosed herein quantifies the copy number and viral load of each and every type present in the sample. In another embodiments, repeated testing of a positive HPV sample at different time intervals may indicate virus persistence or clearance based on copy number or viral load.

In various embodiments of the present disclosure, the compatibility and non-compatibility score of the selected primers are calculated based on different factors of target amplicon GC content, target amplicon melting temperature, target amplicon heterozygosity rate, complementary rate of the candidate primer for the target region; candidate primer size, target amplicon size and amplification efficiency and off-target rate. The selected target-specific primers can hybridize to the nucleic acid target and selectively amplify the target regions. In various embodiments, the test sample is from a subject or individual that is suspected to have an infection or disease, or an increased risk for an infection or disease; and wherein one or more of the target nucleic acid comprise a sequence at the target region associated with an infection or disease or increased risk of an infection or disease. In some embodiments, information about the detected infectious type or species related to disease can be used for disease management.

In one embodiment, the method disclosed herein can be used to detect HPVs and STIs in a sample. In some embodiments, the candidate primers contact the nucleic acid sample; wherein the forward strand and reverse strand target-specific primers hybridize to target regions (if present in the sample), where the nucleic acid sample may have HPV and STI or is suspected to have HPV and STI, amplifying a plurality of target nucleic acids (if infections are present); subjecting the amplicons to next-generation sequencing; and analyzing the sequence data by a software algorithm. In some embodiments, the detected infections can be clinically actionable. In some embodiments, detected infections can be associated with drug resistance. In some embodiments, detection, identification and quantitation of HPVs and STIs can be related with disease, pre-cancer or cancer. In some embodiments, the biological sample can be screened for cancer. In some embodiments, biological sample from the diseased or healthy subject can be whole genomic DNA or formalin-fixed paraffin-embedded tissue (FFPE).

In one aspect, the method and composition disclosed herein is designed to detect, identify and quantify target nucleic acids in a sample that may contain HPVs or STIs. In some embodiments the disclosed method comprises the steps of: 1) contacting the nucleic acid targets in a sample with primers, wherein forward strand and reverse strand target-specific primers hybridize to different target regions in the test reaction; 2) amplifying the target nucleic acids under optimal amplification conditions to determine presence or absence of HPVs and STIs; 3) sequencing the amplified products by NGS; and 4) analyzing and quantitatively measuring the generated sequence reads by a mapping-and-counting algorithm.

In some embodiments, the nucleic acid sample comprises genomic DNA. In some embodiments, the sample comprises nucleic acid molecules obtained from urine, tissue, saliva, biopsies, sputum, swabs, surgical resections, cervical swabs, tumor tissue, fine needle aspiration (FNA), scrapings, swabs, mucus, semen, other non-restricting clinical or laboratory obtained samples.

In another aspect, the present disclosure is directed to kits comprising target-specific primers for amplifying target regions of interest of a sample.

In some embodiments, the disclosed method comprises the steps of: performing one-step multiplex PCR; and sequencing the resulting amplicons by NGS. In some embodiments, the method further comprises the step of quantifying the copy number of each type or species, allowing for maximum type sensitivity and minimal sequencing reads. In certain embodiments, the samples are obtained from subjects with multiple co-infections. In some embodiments, the method's analytical sensitivity is 20 copies for each virus or species in a sample; the highly multiplex PCR detects 27 HPVs and 13 STIs with minimal primer-primer interactions. In some embodiments, the method comprises the step of performing single-reaction, single-step multiplex PCR. The method has easy workflow and up to tens of thousands of samples can be sequenced by a single NGS sequencing run.

In some embodiments, the disclosed method comprises the use of two internal controls for each sample in the reaction test, wherein the first internal control is a housekeeping gene and monitors amplification and acts as normalization and qualification control, and wherein the second internal control is a polymorphic gene comprising a sequence that is unique for each individual, acting as cross-contamination control. In some embodiments, the HPV and STI test reaction comprises two internal controls for each sample. In some embodiments, the HPV and STI test reaction comprises primers for amplification of the two internal controls.

In some embodiments, the disclosure relates to methods, compositions and kits for application of multiplex target amplification and target enrichment of HPVs and STIs prior to downstream analysis such as next-generation sequencing. The method relies on using a plurality of target-specific primers and target enrichment amplification in a DNA sample that is suspected to have HPVs and STIs. The HPV-STI target-specific primers amplify the target nucleic acids under optimal conditions in presence of amplification reagents such as polymerase and dNTPs to at least amplify one or more nucleic acid targets of interest.

In some embodiments, the disclosure relates to a composition comprising a plurality of target-specific primers that contact the target sequences of HPVs, STIs and internal controls in the sample and have complementary sequences to one or more (non-limiting) HPVs and STIs mentioned below: high-risk HPV-16, 18, 31, 33, 35, 39, 45, 51, 52, 56, 58, 59, 66, 68a, 68b, 26, 53, 82 and low-risk HPV-6, 11, 40, 42, 43, 44, 55, 61, 81, 83 and *Chlamydia trachomatis* (CT), *Treponema pallidum* (TP), *Mycoplasma genitalium* (MG), *Trichomonas vaginalis* (TV), *Neisseria gonorrhoeae* (NG), Herpes simplex virus type 1 (HSV-1), Herpes simplex virus type 2 (HSV-2), *Mycoplasma hominis* (MH), *Ureaplasma urealyticum* (UU), *Ureaplasma parvum* (UP), Varicella-zoster virus (VZV), *Haemophilus ducreyi* (HD), Lymphogranuloma venereum (LGV).

In some embodiments of the disclosed method, the primer design algorithm selects the candidate target-specific primers based on steps of: 1) extracting genomic sequences around each targeted variant position; 2) for each variant in the target sequence, designing target-specific forward strand and reverse strand target-specific primers with proper GC content, $T_m$, and varying distances from each targeted region; 3) for each primer, searching target genome sequences for off-target matches; filter primers and keep those primers that pass the off-target threshold; 4) searching the 3'-end portion of each primer for complementary matches with primer sequences of the set; filter primers progressively where the primer with its 3'-end having most complementary matches is removed first; and 5) synthesizing primers and running the entire wet-lab experiment using next-generation sequencing; calibrate the performance of each primer and filter out primers of undesired performance. In some embodiments, the primer selection procedure steps 2 to 4 and steps 2 to 5 are repeated until each target variant is covered by at least one forward strand target-specific primer and one reverse strand target-specific primer in the primer set.

In various embodiments of any of the aspects of this disclosure, the methods and compositions feature multiplex amplification and target enrichment of target nucleic acid regions of HPVs, STIs and internal controls. In some embodiments, the disclosed method comprises the steps of: 1) contacting target-specific primers with target nucleic acid sequences in presence of barcoded universal primers and hybridizing to target nucleic acid sequences in the sample; 2) subjecting the test reaction to amplification under optimal amplification conditions; 3) pooling together the amplified products from each individual sample; 4) subjecting a portion of the pooled amplified products to bead cleanup to remove unconsumed primers and primer-dimers and create enriched amplified products; 5) subjecting a portion of enriched amplified products to standard normalization and quantification; and 6) sequencing the amplicon by next-generation sequencing.

Figure 1:
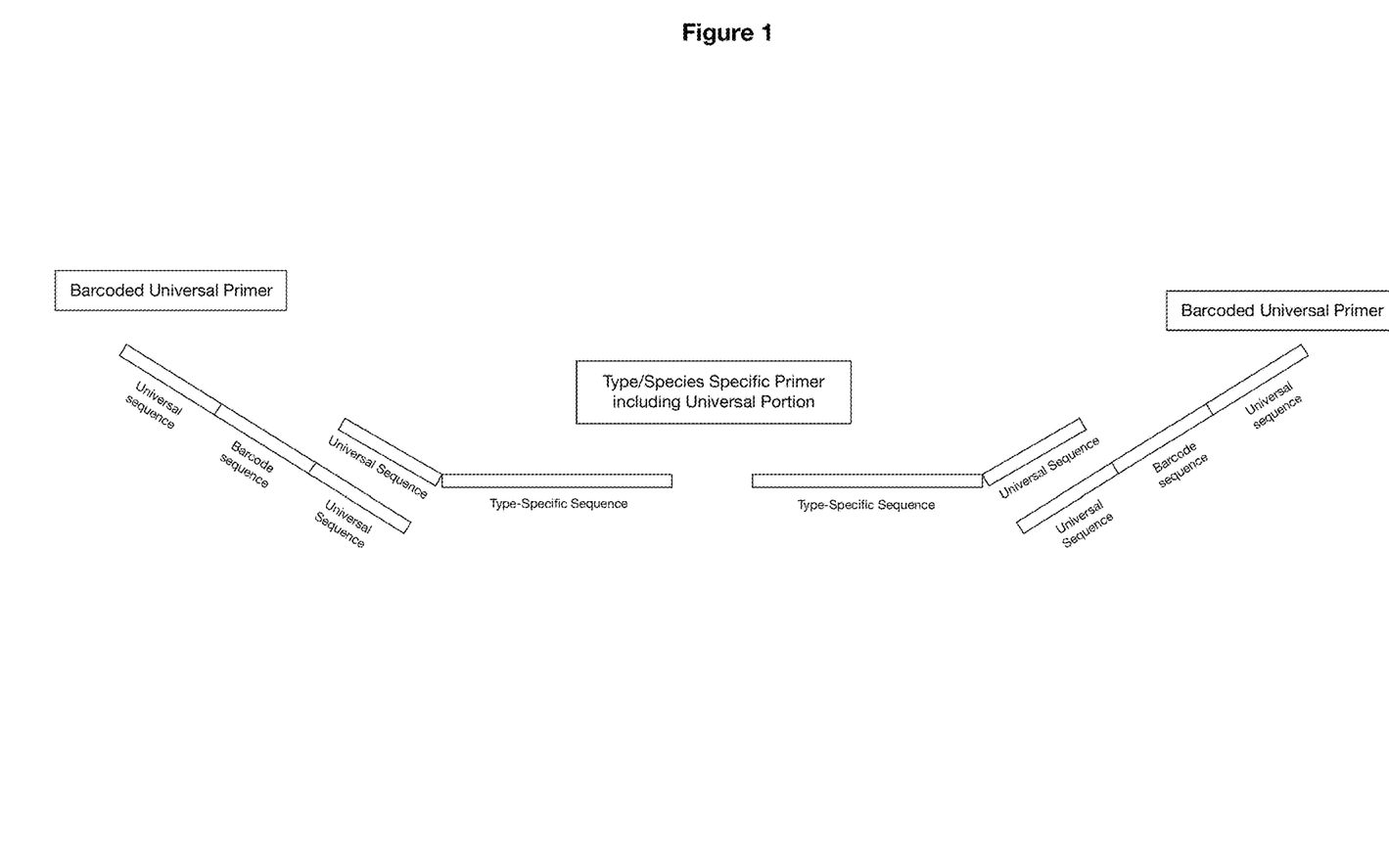
FIG. 1 depicts an illustration of a type/species-specific primer and a barcoded universal primer.

In one embodiment, the barcoded universal primers comprise: a) a universal priming portion at the 3'-end; b) a barcode portion in the middle; and c) a universal priming portion at the 5'-end (FIG. 1). In one embodiment, each target-specific primer comprises a specific sequence portion directed to target nucleic acid sequence and a universal priming portion.

In some embodiments, the composition comprises a plurality of target-specific primers wherein at least one target-specific primer is at least 90% identical to any one of the nucleic acid targets. In some embodiments, the composition comprises a plurality of target-specific primers having a sequence identity of at least 91%, 92%, 93%, 94%, 95%, 96%, 97%, 98% or 99% to the nucleic acid targets in the sample.

In some embodiments, the disclosure relates to a composition comprising a plurality of target-specific primers wherein the sequence complementary to target nucleic acid of interest is about 15 to 40 bases in length.

In some embodiments, the disclosure relates to a composition of pre-calculated design of target primers that generate minimal cross-hybridization or primer-primer interactions with other target specific primers in the composition. In some embodiments, the primers in the composition are designed to avoid non-specific priming that can lead to non-specific amplifications. In some embodiments, the amplification conditions such as annealing temperature, annealing duration and primer concentrations can be adjusted to minimize amplification artifacts such as primer-dimers.

In some embodiments, the disclosure relates to a method or composition comprising a plurality of target-specific primers having minimal cross-hybridization to non-specific sequences present in the sample. In some embodiments, such cross-hybridization to non-specific targets could be monitored and evaluated by downstream analysis such as next-generation sequencing.

In some embodiments, the disclosure relates to a method or composition comprising a plurality of target-primers having minimal self-complementary structure. In some embodiments, the composition comprises at least one target-specific primer that do not form a secondary structure, such as hairpins or loops. In some embodiments, the composition comprises a plurality of target-specific primers that the majority, or potentially all the target-specific primers do not form secondary structures such as hairpins and loops.

In some embodiments, the target nucleic acid is obtained from a biological sample from a subject. In some embodiments, the sample comprises proteins, cells, fluids, biological fluids, preservatives, and/or other substances. In certain embodiments, the sample comprises urine, tissue, saliva, biopsy, sputum, cheek swab, formalin-fixed paraffin-embedded material (FFPE), cervical swab, cervical brush, tumor tissue and fine needle aspiration (FNA) and cervical biopsy.

In some embodiments, the target amplification products are sequenced by next generation sequencing on current state-of-art next-generation sequencing technologies or platforms such as Illumina platforms (reversible dye-terminator sequencing), 454 pyrosequencing, Ion Semiconductor sequencing (Ion Torrent), PacBio SMRT sequencing, Qiagen GeneReader sequencing technology, and Oxford Nanopore sequencing. In some embodiments, the disclosed method is not limited to these next-generation sequencing technologies examples and can be applied to new sequencing innovations.

In certain embodiments, the foregoing methods may be performed at multiple time points.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure relates to methods and compositions for detection, identification and quantification of 27 HPVs and 13 STIs in a single multiplex amplification step. The quantification of certain HPV genotypes may serve as predictor of pre-cancer and cancer, and STIs may serve as predictor of sexually transmitted disease (STD) in clinical specimens. The disclosed method utilizes NGS for sequence analysis of amplified products. The present disclosure also discloses kits, systems, and software. The following examples, applications, descriptions and content are exemplary and explanatory, and are non-limiting and non-restrictive in any way.

Developing a highly multiplex PCR for a sample that contains both host DNA and viral/species DNA with accurate and high copy number sensitivity remains a challenge in the art. The present disclosure relates to an NGS-based assay that combines balanced type-specific multiplex amplification of viral/species DNA and sensitive copy number quantification, and balanced sequencing reads of each type/species. The disclosed assay also comprises a unique feature of two internal controls. The first internal control is a human housekeeping gene that checks amplification and at the same time is used for quantification of viral load or type/species copy number. The second internal control is a human polymorphic gene containing unique sequence for every individual, which monitors cross-contamination. The second control can accurately monitor low traces of contamination and serves as PCR contamination prevention measurement.

All scientific terms used herein have the same meaning as commonly used and understood by one of ordinary skill in the art. Examples, materials, methods, figures and tables are illustrative only and not intended to be limiting.

As used herein, "amplification conditions" means conditions suitable for amplification using polymerase chain reaction. The polymerase chain reaction can be multiplex PCR. Amplification conditions include, but are not limited to, the examples provided in Examples 1 and 2 disclosed herein.

As used herein, "barcoded universal primer" means a universal primer comprising a barcode sequence and at least one universal sequence. See, e.g., FIG. 1.

As used herein, "bead cleanup" means the use of bead-based purification wherein beads are configured to bind to one or more targets. As known to those of skill in the art, bead cleanup may use positive selection (i.e., the bead is configured to capture the target of interest) or negative selection (i.e., the bead is configured not to capture the target of interest). Various may be used, as known in the art, such as streptavidin beads or magnetic beads. One example of beads is SPRI beads, as disclosed in examples 1 and 2 herein.

As used herein, "compatibility score" means a score for a potential forward strand target-specific primer or reverse strand target-specific primer that is calculated based on different factors of target amplicon GC content, target amplicon melting temperature, target amplicon heterozygosity rate, complementary rate of the candidate primer for the target region; candidate primer size, target amplicon size, primer-primer interactions and amplification efficiency and off-target rate.

As used herein, "CT" means *Chlamydia trachomatis*.

As used herein, "dsDNA" means double stranded DNA.

As used herein, "FFPE" means formalin-fixed paraffin-embedded.

As used herein, "FNA" means fine needle aspiration.

As used herein, "forward strand" means one strand of a dsDNA sample.

As used herein, "forward strand target-specific primer" means a primer configured to bind to a target sequence on the forward strand.

As used herein, "GC content" means guanine-cytosine content.

As used herein, "HPV" means human papillomavirus.

As used herein, "HSV1 and HSV2" means Herpes Simplex 1 and 2.

As used herein, "MG" means *Mycoplasma genitalium*.

As used herein, "MH" means *Mycoplasma hominis*.

As used herein, "NG" means Neisseria gonorrhoeae.

As used herein, "NGS" means next-generation sequencing.

As used herein, "PCR" means polymerase chain reaction.

As used herein, "reverse strand" means a second strand of a dsDNA sample that is complementary to the forward strand.

As used herein, "reverse strand target-specific primer" means a primer configured to bind to a target sequence on the reverse strand.

As used herein, "species specific primer" means a primer configured to bind to a target specific to a particular species.

As used herein, "target-specific primer" means a primer configured to bind to a specific target. In some embodiments, a target-specific primer may be a type-specific primer. In some embodiments, a target-specific primer may be a species-specific primer.

As used herein, "type-specific primer" means a primer configured to bind to a target specific to a particular HPV genotype.

As used herein, "universal sequence" means a sequence configured to be targeted by a universal sequence primer.

As used herein, "UP" means Ureaplasma parvum.

The present disclosure describes methods, compositions and kits for amplification and enrichment of specific and known sequence HPV and STI targets for determining the nucleotide sequence. The following examples, applications, descriptions and content are exemplary and explanatory, and are non-limiting and non-restrictive in any way.

The present disclosure relates to selective amplification of 27 HPVs, 13 STIs and two internal controls, followed by detection, identification and quantification with NGS. The assay detects the following HPV types and STI species: high-risk HPV-16, 18, 31, 33, 35, 39, 45, 51, 52, 56, 58, 59, 66, 68a, 68b 26, 53, 82 and low-risk HPV-6, 11, 40, 42, 43, 44, 55, 61, 81, 83 and *Chlamydia trachomatis* (CT), *Treponema pallidum* (TP), *Mycoplasma genitalium* (MG), *Trichomonas vaginalis* (TV), *Neisseria gonorrhoeae* (NG), Herpes simplex virus type 1 (HSV-1), Herpes simplex virus type 2 (HSV-2), *Mycoplasma hominis* (MH), *Ureaplasma urealyticum* (UU), *Ureaplasma parvum* (UP), *Varicella-zoster virus* (VZV), *Haemophilus ducreyi* (HD), *Lymphogranuloma venereum* (LGV).

Figure 2:
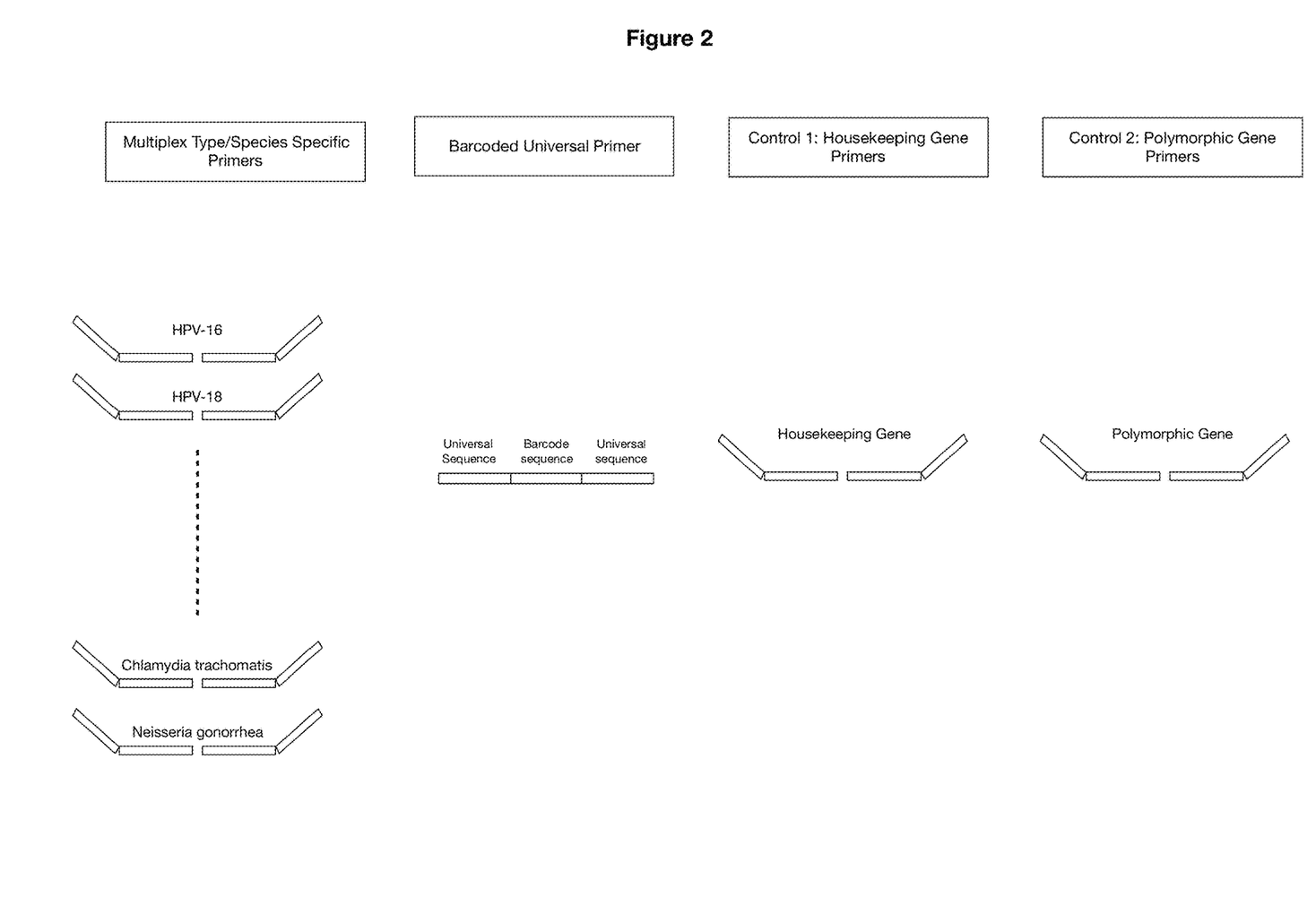
FIG. 2 depicts an illustration of the primer component of a single PCR test reaction, which comprises: 1) type/species specific primer pair (27 HPV primer pairs and 13 STI primer pairs); 2) barcoded universal primer, which comprises a universal sequence portion on 3'-end, a barcode sequences in the middle and a universal sequence portion on 5'-end; 3) housekeeping primer pair; and 4) polymorphic gene primer pair.

The disclosed method offers many advantages that are uniquely composed together including, but not limited to: 1) single reaction PCR; 2) one-round of highly multiplex PCR covering a wide range of HPVs and STIs; 3) dual-index barcoding (barcodes on both ends of each amplicon) to minimize cross-contamination; 4) type/species-specific amplification allowing uniform amplification of all HPVs and STIs; 5) quantification of each individual type/species in the sample, which has clinical value for disease management; 6) a human housekeeping gene as internal control for each sample in each test reaction to monitor amplification and serve as a normalization factor for quantification; 7) a human polymorphic gene as internal control for each sample in each test reaction to monitor cross-contamination; 8) extended typing of all types and species which has clinical significance for monitoring infections, treatment and prevention of disease and cancer; 9) suitable for high throughput scales, where up to tens of thousands of samples can be sequenced in one single sequencing run; 10) the method can be used for screening, detection, identification, typing as well as epidemiological studies and research all at once; and 11) fast, simple and easy automation. See, e.g., FIG. 2.

The main idea for cervical cancer screening is detection of pre-cancer and cancer and not transient HPV infections, which may result in overtreatment and unnecessary follow-ups, treatment and medical procedures that are costly. About 90% of all the colposcopy procedures are overtreatment. Quantification of each HPV type and determining the viral load allows to detect individuals who are at higher risk for development of cancer.

Figure 3:
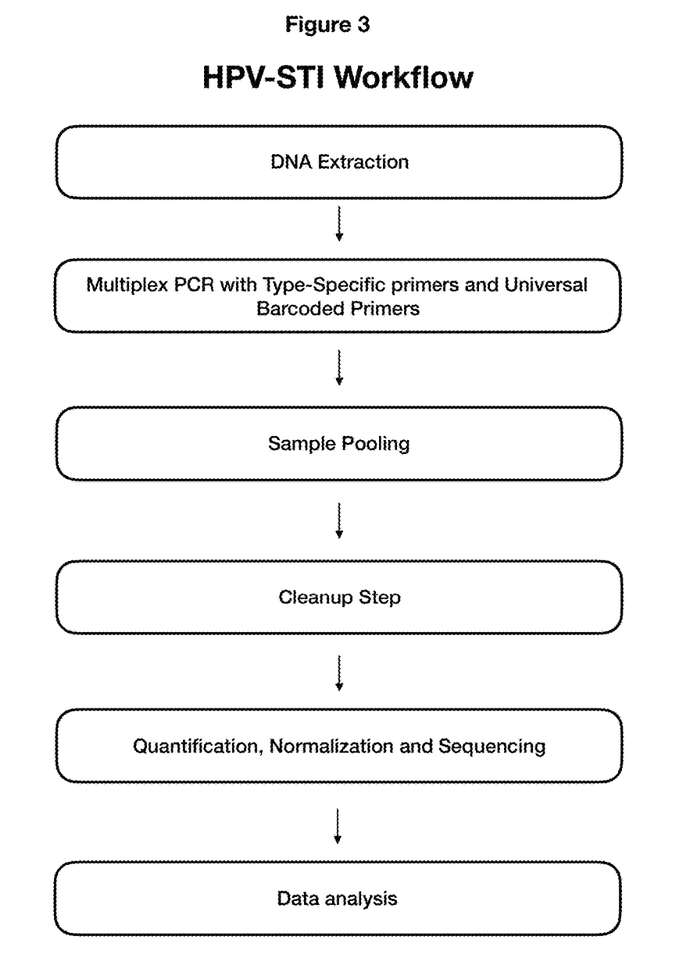
FIG. 3 illustrates the workflow of HPV-STI assay.
Figure 4:
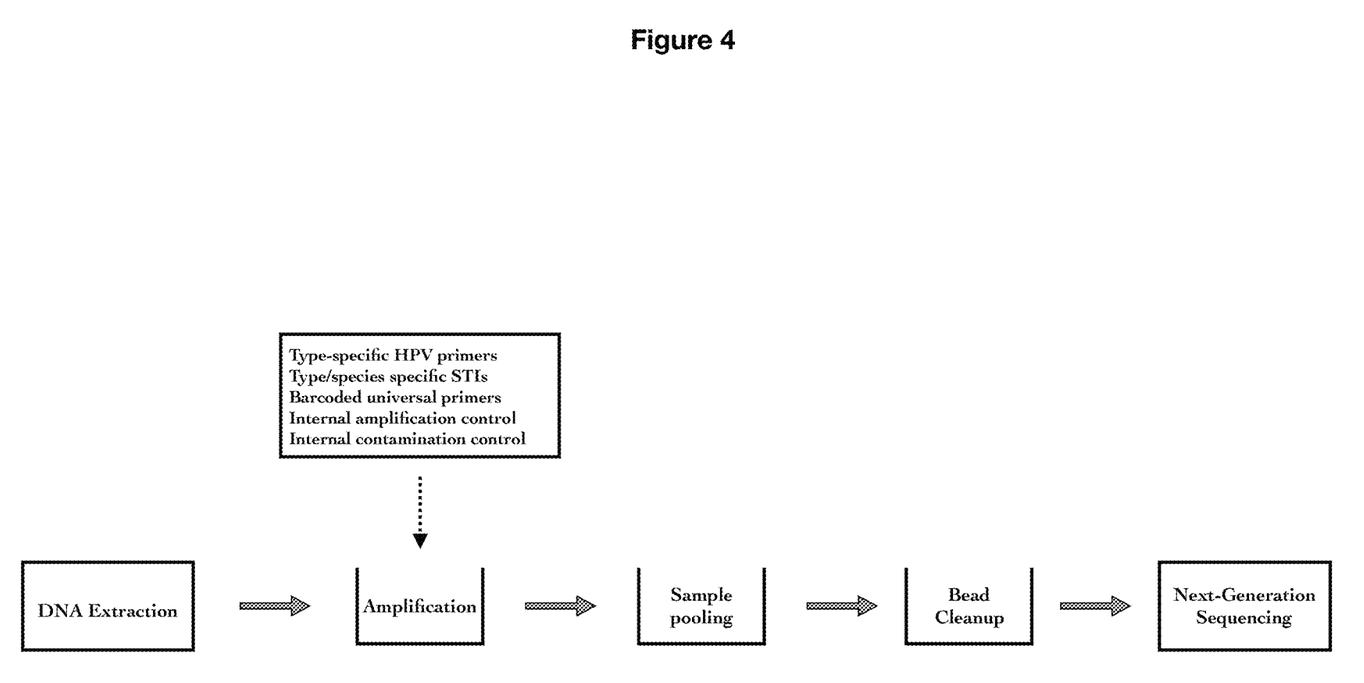
FIG. 4 depicts an illustration of the method.

Herein described is a method of multiplex amplification and target enrichment for HPVs, STI, and internal controls which are analyzed by NGS. In various embodiments of any of the aspects of the present disclosure, the methods and other compositions feature multiplex amplification and target enrichment of target nucleic acid regions HPVs, STIs and internal controls. In some embodiments, the disclosed method comprises the steps of: 1) contacting target-specific primers with target nucleic acid sequences in the presence of barcoded universal primers and hybridizing to target nucleic acid sequences in the sample; 2) subjecting the test reaction to amplification under optimal amplification conditions; 3) pooling together the amplified products from each individual or subject sample; 4) a portion of the pooled amplified products are subjected to bead cleanup to remove possible unconsumed primers and primer-dimers to create enriched amplified products; 5) subjecting a portion of enriched amplified products to standard normalization and quantification; and 6) sequencing the amplicon by next-generation sequencing. See, e.g., FIGS. 3-4.

In one embodiment, the barcoded universal primers comprise: a) a universal priming portion at the 3'-end; b) a barcode portion in the middle; and c) a universal priming portion at the 5'-end (FIG. 1). In one embodiment, each target-specific primer comprises a specific sequence portion directed to target nucleic acid sequence and a universal priming portion.

In some embodiments, the present disclosure provides methods, compositions and kits to detect more than one HPV and STI strain/type/species in a single reaction container.

In some embodiments, the disclosed method utilizes one round of multiplex PCR in one single test reaction for each subject, which minimizes DNA cross-contamination and extra steps in the workflow. In general, methods using more than one round of PCR are vulnerable to DNA cross-contaminations, resulting in accurate results.

Figure 5:
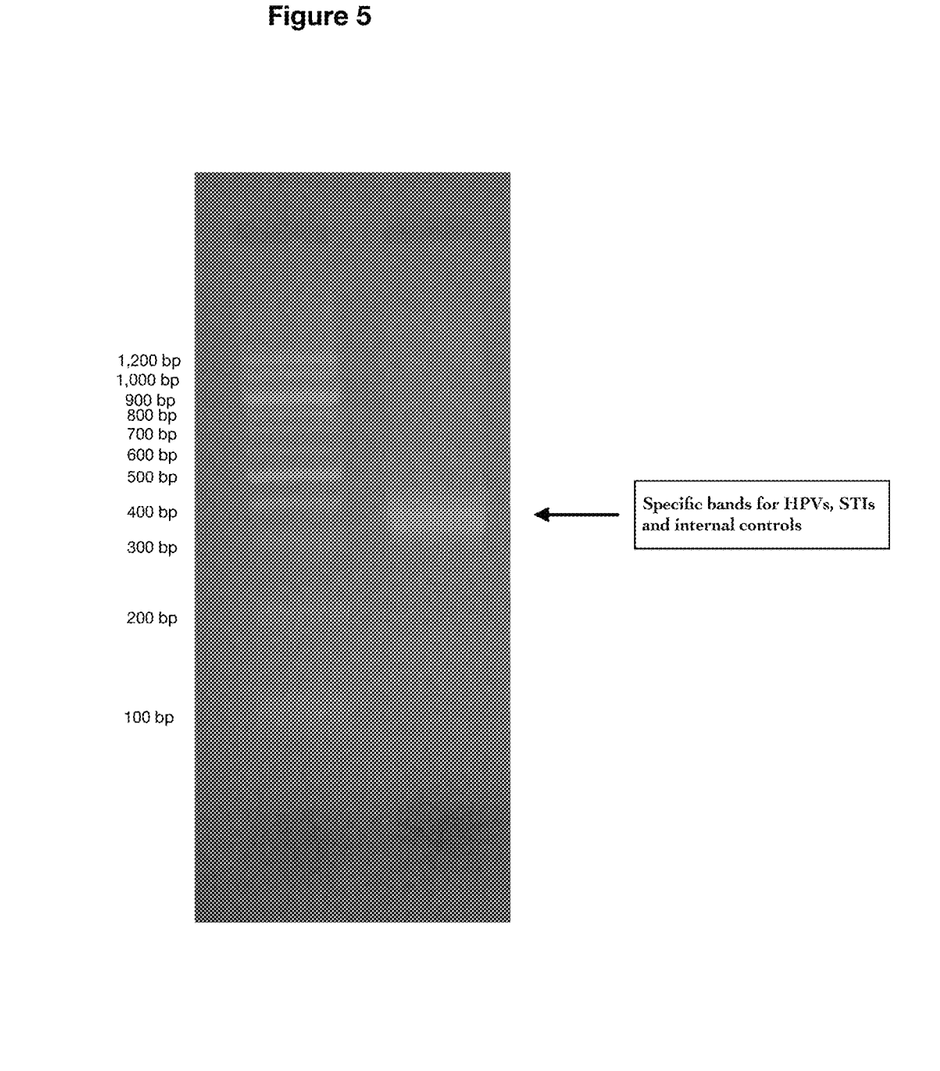
FIG. 5 shows the image of a stained agarose gel. The band shows all samples pooled together and run on gel electrophoresis. The amplicon band comprises internal controls and HPV and STI amplification. The band is indicated with an arrow.

In some embodiments, the disclosed method comprises the use of a plurality of type/species-specific primers for clinically relevant HPVs, STIs and two internal controls (amplification/quantification control and cross-contamination control) for each subject sample in each test reaction. See, e.g., FIG. 5. In some embodiments, the disclosed method is a highly multiplex HPV-STI detection panel, covering an unprecedented and unparalleled wide range HPVs and STIs in a single reaction and one round of PCR. In some embodiments, the multiplex type/species-specific amplification allows a significantly more balanced and uniform amplification of each type or species particularly when the sample contains multiple co-infections, without any concern for type-suppression.

In some embodiments, the disclosed method comprises the use of a housekeeping gene as internal control for each subject in each test reaction, which checks amplification and is used as normalization factor for quantification of viral load or copy number of each type/species for each sample in each test reaction. In some embodiments, the method can quantify multiple types or species in a multiple co-infected sample in one test reaction. In some embodiments, the quantification of copy number or viral load of each type/species may have clinical value for detection of pre-cancer, cancer and disease. In some embodiments, the quantification of copy number or viral load of each type/species may have clinical significance for treatment, follow-ups and necessary medical procedures.

In some embodiments, the disclosed method comprises the use of a polymorphic gene as internal control for each subject in each test reaction, which checks and monitors for cross-contamination in each sample in each test reaction. In some embodiments, the sequence of the polymorphic gene is unique for each human subject and presence of other sequences of the polymorphic gene other than the subject's polymorphic gene sequence shows cross-contamination.

In some embodiments, the disclosed method comprises the use of a dual barcoding index, wherein the amplicon is barcoded by universal barcoded primers on both ends, minimizing cross-contamination and as well as dual confirmation of a barcode in case of amplification errors in early stages of PCR.

In some embodiments, the disclosed method comprises the use of next-generation sequencing for detection, identification and quantification HPVs and STIs. In certain embodiments, target DNA sequences are amplified and sequenced to reveals the strain, HPV type or species present in a sample.

In some embodiments, the amplification conditions such number of cycles, annealing temperature, annealing duration, extension temperature and extension duration are adjusted to optimal conditions for amplification. In some embodiments, number of cycles, the amplification conditions such annealing temperature, annealing duration, extension temperature and extension duration are adjusted to optimal conditions for amplification based on the commercial DNA polymerase instructions.

In some embodiments, the nucleic acid sample comprises genomic DNA. In another embodiment, the sample comprises nucleic acid molecules obtained from cervix by a cytobrush. In another embodiment, the sample can be a self-sampling specimen. In another embodiment, the sample comprises nucleic acid molecules obtained from anal swab or brush. In another embodiment, the sample comprises nucleic acid molecules obtained from FFPE or archived DNA samples. In some embodiments, the sample comprises nucleic acid molecules obtained from saliva. In some embodiments, the sample comprises nucleic acid molecules obtained from urine, tissue, saliva, biopsies, sputum, swabs, formalin-fixed paraffin-embedded material (FFPE), surgical resections, cervical swabs, tumor tissue, fine needle aspiration (FNA), scrapings, swabs, mucus, urine, semen, and other non-restricting clinical or laboratory obtained samples.

In some embodiments, the nucleic acid sample obtained can be from an animal such as a human or mammalian subjects. In another embodiment, the nucleic acid sample obtained can be from a non-mammalian subject such as bacteria, virus, fungi, and plant.

In some embodiments, the disclosure relates to target amplification of at least one target sequence from a biological sample in a normal or diseased subject. In some embodiments, the disclosure relates to the specific and selective target amplification of at least one target sequence and detection and identification of HPVs and STIs in the nucleic acid biological sample that can cause disease. In some embodiments, the detected HPV or STI can be a clinically actionable infection. In some embodiments, the biological sample can be screened for sexually transmitted diseases (STD), pre-cancer and cancer.

In some embodiments, the target-specific primers comprise a plurality of primers that are designed to amplify selectively HPVs and STIs target nucleic acid sequences; the amplification range differs due the size of fragments and positions of primers on the nucleic acid fragment and the size can vary in the range. In some embodiments, the target-specific primers comprise a plurality of primer that are selectively designed to amplify target nucleic acid sequences, where the amplified target nucleic acid sequences can vary in length from one another by no more than 90%, no more than 70%, no more than 50%, no more than 25% or no more than 10%.

In some embodiments, the disclosed method relates to target enrichment by multiplex target-specific polymerase chain reaction (PCR), which comprises the steps of contacting the nucleic acid targets with a plurality of target-specific primers in the presence of barcoded universal primer and PCR reagents such as DNA polymerase, dNTPs and reaction buffer; given the optimal conditions of temperature and time for denaturation, annealing and extension, the primers hybridize to complementary target nucleic acid sequences and are extended. In some embodiments, the amplification steps can be performed in any order. In some embodiments, amplification steps, purification steps and cleanup steps could be added or removed upon optimization for optimal multiplex target amplification for downstream processes.

In some embodiments, the described method uses polymerase chain reaction (PCR) and DNA polymerase as one of the components in the reaction. In some embodiments, there are a wide selection of DNA polymerases, which feature different characteristics such as thermostability, fidelity, processivity and Hot Start. The method can use a DNA polymerase with one or more of these features depending on the application. In some embodiments, the concentration of DNA polymerase for multiplex PCR can be higher than single-plex PCR.

In some embodiment, the method disclosed herein uses amplification of target nucleic acid sequences using multiplex polymerase chain reaction, wherein more than one target sequence is amplified in a test reaction. In some embodiments, the amount of nucleic acid sample needed for multiplex amplification can be about 1 ng. In some embodiments, the amount of nucleic acid material can be about 5 ng, 10 ng, 50 ng, 100 ng or 200 ng.

In some embodiments, the disclosed method herein uses amplification of target nucleic acid sequences using multiplex polymerase chain reaction, wherein more than one target sequence is amplified in a test reaction. The state-of-art polymerase chain reaction is performed on a thermocycler and each cycle of PCR comprises of denaturation, annealing and extension. Each cycle of PCR comprises at least denaturation step, one annealing step and one extension step for extension of nucleic acids. In some embodiments, annealing and extension can be merged. In some embodiments, the method disclosed herein comprises 25 to 35 cycles of PCR. Each cycle or set of cycles can have different durations and temperatures, for example the annealing step can have incremental increases and decreases in temperature and duration or the extension step can have incremental increases and decreases in temperature and duration. In some embodiments, duration can have decreases or increases in 5 seconds, 10 seconds, 30 seconds, 1 minute, 2 minutes, 4 minutes, 8 minutes or greater increments. In some embodiments, temperature can have decreases or increases in 0.5, 1, 2, 4, 8, or 10° Celsius increments.

In some embodiments of the present disclosure, the target-specific primers comprise a nucleotide modification in 3'-end or 5'-end or across the sequence. In some embodiments, the length of target-specific portion of the primer can be 15 to 40 bases. In some embodiments, the $T_m$ of each target-specific primer can be about 55° C. to about 72° C.

In some embodiments, the disclosure features a target enrichment and multiplex amplification approach for target specific nucleic acid amplification HPVs and STIs using target-specific primers. In some embodiments, the selected target-specific primers contact and hybridize to target nucleic acid sequences that can be related to disease. In some embodiments, the disease can be a STD, pre-cancer or cancer. In one embodiment, target-specific primers hybridize to nucleic acid sequences in the test reaction, which have different sizes. In some embodiments, amplicon size selection can be used to sequence amplified products of a certain length range. In some embodiments, amplicons of 100 to 250 base pairs range in length can be sequences. In some embodiments, amplicons of 150 to 300 base pairs, or amplicons of 120 to 350 base pairs, or amplicons of 200 to 500 base pairs range or greater length range can be sequenced.

In some embodiments, any of the procedures can be removed or can be repeated. In some embodiments, purification steps can be added for generating optimal results. These procedures are non-limiting and a skilled person of the art can readily add, remove or repeat the steps for optimal results.

The ability to increase the number of target-specific primers in a multiplex PCR allows simultaneous amplification of a large number of nucleic acid targets while decreasing the amount of input DNA, labor and time. This is especially advantageous when the amount of starting input nucleic acid material is limited.

In some embodiments of the disclosed method, the primer design algorithm selects the candidate target-specific primers based on this stepwise procedure: 1) extraction of genomic sequence around each targeted variant position; 2) for each variant in the target sequence, design target-specific forward strand and reverse strand target-specific primers with proper GC content, $T_m$, and varying distances from each targeted variant; 3) for each primer, searching target genome sequences for off-target matches; filter primers and keep those primers that pass the off-target threshold; 4) search the 3'-end portion of each primer for complementary matches with primer sequences of the set; filter primers progressively where the primer with its 3'-end having most complementary matches is removed first; 5) synthesize primers and run the entire wet-lab experiment comprising next-generation sequencing; calibrate the performance of each primer and filter out primers of undesired performance.

In some embodiments, the primer selection procedure steps 2 to 4 and steps 2 to 5 are repeated until each target variant is covered by at least one forward strand target-specific primer and one reverse strand target-specific primer in the primer set.

In some embodiments, the disclosure features a primer design algorithm that eliminates low compatibility primers that form artifacts such as primer-dimers in a highly multiplexed PCR that inhibit efficient amplification. Such elimination system removes or significantly minimizes the non-productive artifacts such as primer-dimers. Removal of low-compatibility and problematic primers significantly improves the overall performance and efficiency of highly multiplex PCRs in addition to downstream processes such as high throughput sequencing. Artifacts and primer dimers cause significant failure in obtaining optimal sequence results and a significant portion of the sequencing reads can be non-specific and non-informative.

In some embodiments, the primer selection algorithm features a primer compatibility score both in regard to primer-primer interactions and specific target nucleic acid hybridization without non-specific priming or hybridizing to off-target regions. A higher compatibility score for a candidate target-specific primer characterizes specific hybridization to target nucleic acid with no or minimal interaction with other primers in the primer set. Primers that do not meet the compatibility score that is to say are above the minimum threshold are removed. In various embodiments of the disclosed method, a compatibility score is calculated for at least 80, 90, 95, 98, 99, or 99.5% of the possible combinations of candidate primers in the set. The compatibility score in primer selection is calculated based on a number of parameters such as target amplicon GC content, target amplicon melting temperature, target amplicon heterozygosity rate, complementary rate of the candidate primer for the target region; candidate primer size, target amplicon size and amplification efficiency. Due to the fact that several aspects are involved in determining the compatibility score, an average score is calculated based on multiple parameters and average could be variable for particular applications. The primer selection algorithm will keep eliminating the low-compatibility primers, and the elimination process is repeated to equal or below minimum threshold till an optimal selection primer group is achieved that generates a highly multiplex target amplification PCR with no or minimized primer-dimers.

In some embodiments, the primer selection algorithm features a primer compatibility score both in regard to primer-primer interactions and specific target nucleic acid hybridization without hybridizing to off-target regions. The primers that have low compatibility score that is to say above the minimum threshold will be eliminated. However, if there are limitations in primer selection in certain applications, the minimum threshold can be increased to a higher level of second threshold to facilitate primer selection for the primer group. In some embodiments the selection process is repeated until candidate primers are selected that are equal or under the second level of minimum threshold.

In an embodiment, the disclosed method herein features a multiplex amplification and target enrichment by utilizing target-specific primers that contact target HPVs and STIs nucleic acid sequences wherein primer dimers can be reduced or minimized by adjusting different parameters such as duration of annealing steps, increase or decrease of temperature increments combined with number of cycles. In some embodiments, the primer concentrations can be lowered, and annealing temperature and duration can be increased to allow specific amplification (the primers have more time interval to hybridize to target nucleic acids) in addition to reduced or minimal primer-dimers. In some embodiments, the concentration of primers can be 500 nM, 250 nM, 100 nM, 80 nM, 70 nM, 50 nM, 30 nM, 10 nM, 2 nM, 1 nM or lower than 1 nM. In some embodiments, the annealing temperature could be 1 minute, 3 minutes, 5 minutes, 8 minutes, 10 minutes or longer. In some embodiments, the amplification with longer annealing time uses 1 cycle, 2 cycles, 3 cycles, 5 cycles, 8 cycles, 10 cycles or more followed by standard annealing durations.

In one aspect, the disclosed method comprises the step of amplifying selective HPV and STI target regions in a nucleic acid sample. In some embodiments, the method comprises the step of contacting the nucleic acid sample with target-specific primers in presence of barcoded universal primers in a test reaction. In some embodiments, the method comprises the step of determining the presence or absence of target amplification product. In some embodiments, the method comprises the step of determining the sequence of the amplified target products. In some embodiments, less than 50, 40, 30, 20, 10, 5, 0.5, or 0.1% of the amplified products are primer-dimers or artifacts. In one embodiment, there can be more than one set of target specific primers as an example there can be two sets of target-specific primers for two test reactions, 3 sets for 3 test reactions or 5 sets for 5 test reactions or more. In some embodiments for practical reasons such as limitations in primer design or selection, the sample may also be split into multiple parallel multiplex test reactions with multiple sets of target-specific primers.

In various embodiments, concentration of each primer can be 500 nM, 250 nM, 100 nM, 80 nM, 70 nM, 50 nM, 30 nM, 10 nM, 2 nM, 1 nM or lower than 1 nM. In various embodiments, primer concentration of each primer can be between 1 µM and 1 nM, between 1 nM and 80 nM, between 1 nM and 100 nM, between 10 nM and 50 nM or 1 nM and 60 nM. In some embodiments, the GC content of target-specific primers can be between 40% and 70%, or between 30% and 60% or 50% and 80% or 30 and 80%. In some embodiments, primer GC content range can be less 20%, 15%, 10% or 5%. In some embodiments, the melting temperature ($T_m$) of the target-specific primers can be between 55° C. and 65° C., or 40° C. and 72° C., or 50° C. and 68° C. In some embodiments, the melting temperature range of the primers can be less 20° C., 15° C., 10° C., 5° C., 2° C. or 1° C. In some embodiments, the length of the target-specific primers can be between 20 and 90 bases, 40 and 70 bases, 20 and 40 bases or 25 and 50 bases. In some embodiments, the range of length of the primers can be 60, 50, 40, 30, 20, 10, or 5 bases. In some embodiments, the 5'-region of the target-specific primer is a universal priming site that are not complementary or specific for any target nucleic acid regions.

In one aspect, the present disclosure is directed to a kit that comprises target-specific primers in a group; the primers are designed and selected based on criteria described to have minimal primer-primer interactions or non-specific priming. In another embodiment, the kit can be formulated for detection, screening, diagnosis, prognosis and treatment of disease such as sexually transmitted diseases, pre-cancer and cancer.

In some embodiments, the disclosed method comprises the steps of: 1) contacting target-specific primers with target nucleic acid sequences in the presence of barcoded universal primers and hybridizing to target nucleic acid sequences in each sample in the test reaction; 2) subjecting the test reaction to amplification under optimal amplification conditions; 3) pooling together the amplified products from each individual sample; 4) subjecting a portion of the pooled amplified products to bead cleanup to remove possible primer-dimers to create enriched amplified products; 5) subjecting a portion of the enriched amplified products to standard normalization and quantification; and 6) sequencing the amplicon by next-generation sequencing. The method may further comprise additional steps, such as purification.

In one aspect, highly multiplex PCR is utilized for the method disclosed. In some embodiments, between 1 and 10 cycles of PCR can be performed for PCR; in some embodiments between 1 and 15 cycles or between 1 and 20 cycles or between 31 and 25 cycles or between 1 and 30 cycles, between 1 and 35 cycles or more can be performed.

In another embodiment, the disclosed method can be used in a multiplex fashion when amplifying more than two targets and is not limited to any number of multiplexing.

In some embodiments, the amplification product can be sequenced by next-generation sequencing platforms. Next-generation sequencing is referred to non-sanger based massively parallel DNA nucleic acid sequencing technologies that can sequence millions to billions of DNA strands in parallel. Examples of current state of state-of-art next-generation sequencing technologies and platforms are Illumina platforms (reversible dye-terminator sequencing), 454 pyrosequencing, Ion Semiconductor sequencing (Ion Torrent), PacBio SMRT sequencing, Qiagen GeneReader sequencing technology, and Oxford Nanopore sequencing. The present disclosure is not limited to these next-generation sequencing technologies examples.

Sequence reads are first labeled with sample ID, based on barcode sequences. After that, reads are mapped to target reference sequences. Those alignments between sequence read and target reference sequence are filtered with mapping score greater than a predefined cutoff. For each read, only alignment with best mapping score is kept for downstream analysis. The count of sequence reads mapped to a particular species reference sequence is used to proximate the copy number species in a sample. To compare copy numbers among different samples, all read counts are normalized to have the same number of reads for internal control gene GAPDH. Moreover, different concentrations of spike-in standard controls such as plasmids can provide standard curve for quantification of absolute copy numbers of each strain/type/species.

EXAMPLE 1

Analysis of Different HPV Plasmid Type Mixtures and Concentrations Materials and Methods HPV Plasmid Samples: The HPV plasmids were from WHO LabNet international proficiency HPV panel. 26 samples were selected from the panel that included the types HPV-6, 11, 16, 18, 31, 33, 35, 39, 45, 51, 52, 56, 58, 59, 68a and 68b. The samples were either in single type or a mixture of types at varying concentrations based on International Standards to evaluate the sensitivity and type-specificity of detection. The HPV plasmids single type and mixtures types were 100 and 500 copies per pl.

Spiking with human DNA: Prior to amplification, 2 µl of each HPV plasmid sample was mixed with 10 ng human DNA for quantification purposes.

Amplification: One-step multiplex PCR was performed with 27 HPV, 13 STI and two internal controls target-specific primers in the presence of barcoded universal primers, with HPV plasmid DNA, DNA polymerase, dNTP and PCR buffer. The PCR amplification conditions comprise initiation at 95° C. 2 min, 10 cycles of 95° C. 30S, 59° C. 2 min, 72° C. 1 min, 5 cycles of 95° C. 30S, 68° C. 30S, 72° C. 1 min, 15 cycles of 95° C. 30S, 72° C. 1 min 30S and final extension at 72° C. for 10 min.

Sample preparation and next-generation sequencing: All of the 26 amplicons were pooled into one tube. A portion of the samples was then purified with SPRI beads (Beckman Coulter, Calif., USA) according to the manufacturer's instructions. The purified sample concentration was measured with Qubit 3 and the concentration was normalized for sequencing. The library was sequenced with Illumina MiniSeq system using an Illumina Mid Output sequencing kit.

Results: Sequence reads were first grouped on barcode or ID sequences. Sequence reads were mapped to target reference sequences where the alignments of sequence reads and target reference sequences were filtered based on mapping score. To measure copy numbers, all read counts were normalized to have the same number of reads for internal control gene GAPDH. Of the 26 samples, 25 were positive in HPV and genotyped and quantified correctly and one sample was negative for HPV. The results were 100% in accordance with the reference results. The limit of detection was 20 copy numbers.

Figure 6:
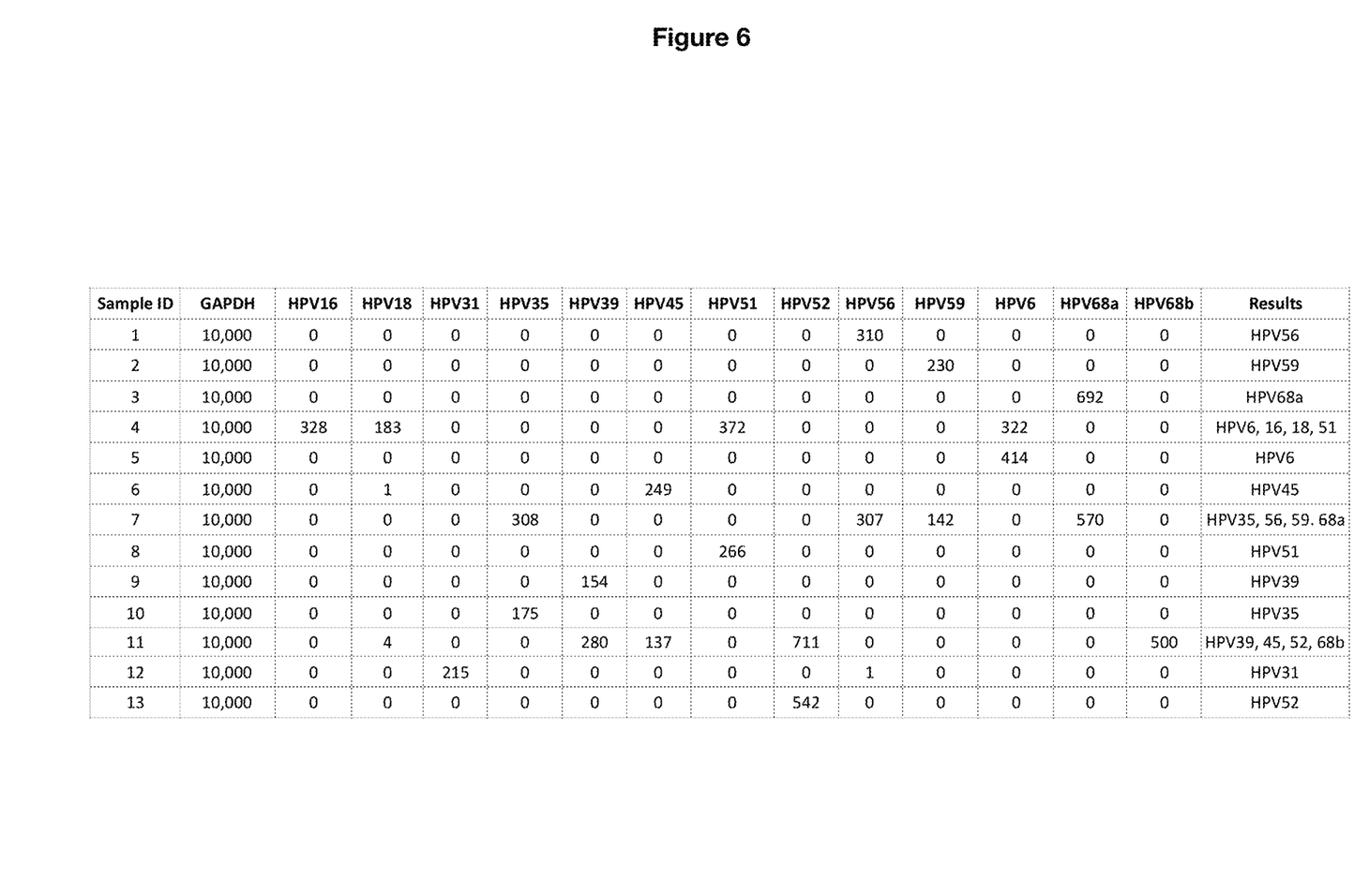
FIG. 6 shows the table from example 1 where different plasmids (single and mixtures) with different concentrations have been sequenced. The numbers indicate copy number, which were normalized to make the GAPDH number 10,000.

Table 1 (FIG. 6) shows different plasmids (single and mixtures) with different concentrations that have been sequenced. The numbers indicate copy number, which were normalized to make GAPDH number to 10,000.

EXAMPLE 2

Detection, Identification and Quantification of HPVs and STIs in Clinical Samples Materials and Methods Clinical samples: 149 DNA samples that had already been tested for HPV were used for the disclosed method. The samples had not been tested for presence of STIs.

DNA extraction: The DNA was extracted by Qiagen Mini DNA kit (Qiagen, Hilden, Germany) according to manufacturer's instructions.

HPV Plasmid Controls: The HPV plasmids HPV-6, 11, 16, 18, 31, 33, 35, 39, 45, 51, 52, 56, 58, 59 and 68 were used as positive control. Prior to amplification, 2 µl of each HPV plasmid sample was mixed with 10 ng human DNA for quantification purposes.

Amplification: One-step multiplex PCR was performed on 175 samples and HPV plasmids with 27 HPV, 13 STI and two internal controls target-specific primers in the presence of barcoded universal primers, sample DNA, DNA polymerase, dNTP and PCR buffer. The PCR amplification conditions comprise initiation at 95° C. 2 min, 10 cycles of 95° C. 30S, 59° C. 2 min, 72° C. 1 min, 5 cycles of 95° C. 30S, 68° C. 30S, 72° C. 1 min, 15 cycles of 95° C. 30S, 72° C. 1 min 30S and final extension at 72° C. for 10 min.

Sample preparation and next-generation sequencing: All of the 175 and HPV plasmids amplicons were pooled into one tube. A portion of the samples was then purified with SPRIbeads (Beckman Coulter, Calif., USA) according to the manufacturer's instructions. The purified sample concentration was measured with Qubit 3 and the concentration was normalized for sequencing. The library was sequenced with Illumina MiniSeq system using an Illumina Mid Output sequencing kit.

Results: Sequence reads were first grouped on barcode or ID sequences. Sequence reads were mapped to target reference sequences where the alignments of sequence reads and target reference sequences were filtered based on mapping score. To measure copy numbers, all read counts were normalized to have the same number of reads for internal control gene GAPDH. All of the HPV plasmids were in agreement with the results. The 175 clinical samples were in agreement with previous typed results, but more genotypes were detected as well as other STIs. The samples had only been tested for HPV and not for other STIs. A portion of the samples revealed the presence of other STIs. All of the samples were quantified based on their copy number. The limit of detection was 20 copy numbers.

Figure 7:
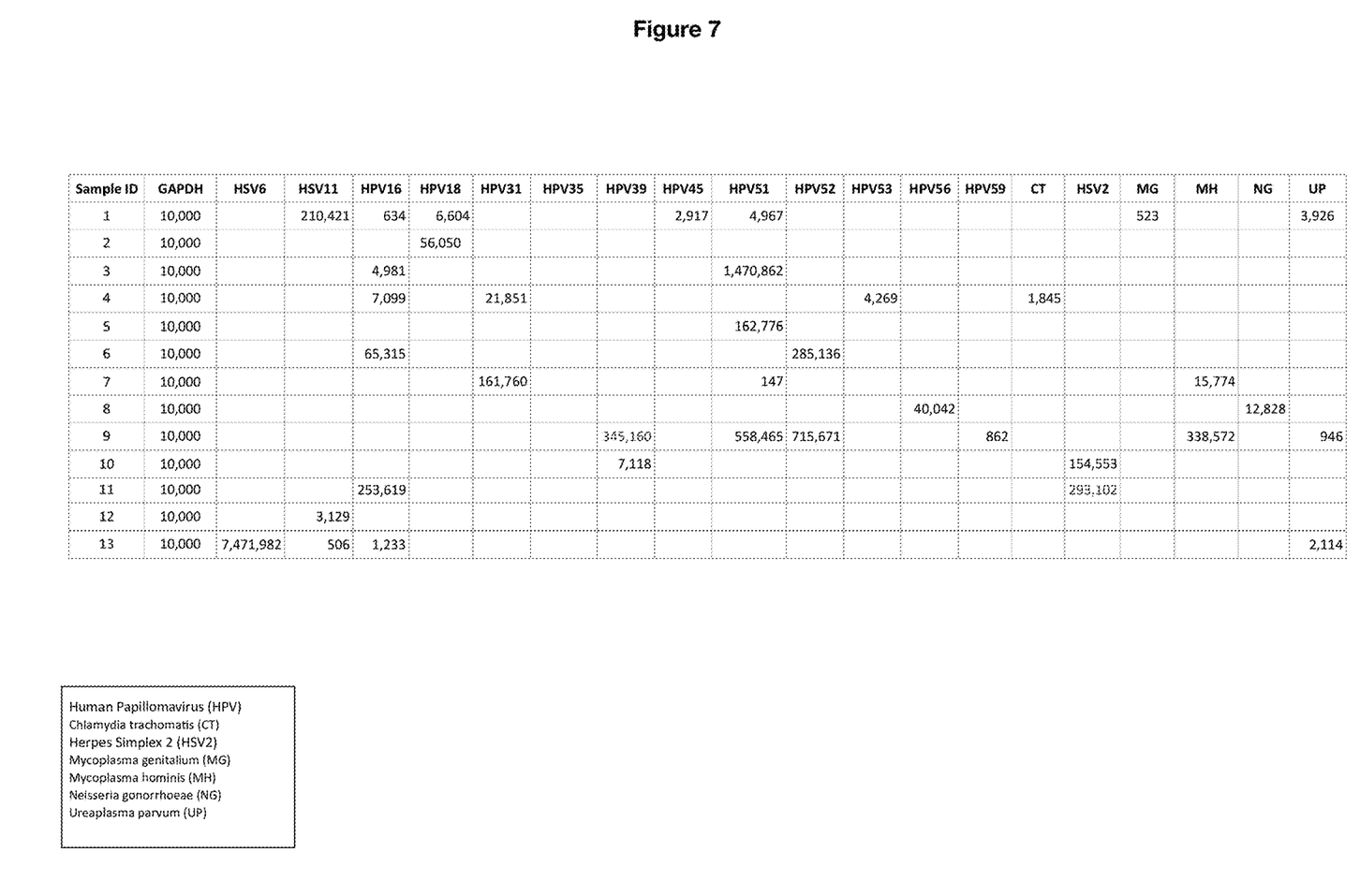
FIG. 7 shows the table from example 2 where samples positive for HPV and STI have been sequenced. The numbers indicate copy number, which were normalized to make the GAPDH number 10,000.

Table 2 (FIG. 7) shows samples positive for HPV and STI that have been sequenced. The numbers indicate copy number, which were normalized to make GAPDH number to 10,000.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

The methodologies and the various embodiments thereof described herein are exemplary. Various other embodiments of the methodologies described herein are possible.

Now, therefore, the following is claimed:

1. A method of screening a sample from each of one or more subjects, comprising the steps of:
   for each sample, hybridizing a plurality of target-specific primers with nucleic acid from the sample in the presence of barcoded universal primers to form a test reaction, wherein at least one target-specific primer is configured to bind to a target sequence specific to sexually transmitted infection and wherein each target-specific primer comprises a specific sequence portion directed to a target nucleic acid sequence and a universal priming portion;
   subjecting each test reaction to amplification conditions to generate amplicons;
   subjecting at least a portion of the amplicons generated from each sample to bead cleanup to form enriched amplicons; and
   sequencing the enriched amplicons, formed from each sample, by next-generation sequencing;
   wherein each barcoded universal primer comprises: a universal priming portion at the 3'-end; a barcode portion in the middle; and a universal priming portion at the 5'-end.

2. The method of claim 1, wherein the sample is obtained from a subject suspected of having or diagnosed with at least one sexually transmitted infection.

3. The method of claim 1, further comprising the step of pooling the enriched amplicons from each sample prior to sequencing.

4. The method of claim 1, further comprising the step of quantifying each type and species in each sample after sequencing the enriched amplicons.

5. The method of claim 1, wherein the test utilizes a polymorphic gene with unique sequence for every individual as internal control to monitor cross-contamination.

* * * * *